(12) United States Patent
Varis et al.

(10) Patent No.: US 8,967,139 B2
(45) Date of Patent: Mar. 3, 2015

(54) RESPIRATORY CONNECTOR AND ARRANGEMENT FOR CONNECTING AN INSPIRATORY TUBE AND AN EXPIRATORY TUBE TO A MEDICAL APPARATUS

(75) Inventors: Anu Varis, Vantaa (FI); Janne Ranta, Espoo (FI)

(73) Assignee: Carefusion Corporation, San Diego, CA (US)

( * ) Notice: Subject to any disclaimer, the term of this patent is extended or adjusted under 35 U.S.C. 154(b) by 1581 days.

(21) Appl. No.: 12/111,682

(22) Filed: Apr. 29, 2008

(65) Prior Publication Data

US 2009/0266357 A1    Oct. 29, 2009

(51) Int. Cl.
*A61M 16/08* (2006.01)
*A61M 16/00* (2006.01)
*A61M 16/10* (2006.01)

(52) U.S. Cl.
CPC ....... *A61M 16/1055* (2013.01); *A61M 16/0816* (2013.01); *A61M 16/0858* (2014.02); *A61M 16/1065* (2014.02); *A61M 16/107* (2014.02); *A61M 2016/0027* (2013.01); *A61M 2230/10* (2013.01); *A61M 2230/60* (2013.01)
USPC ............. 128/202.27; 128/205.27; 128/204.18

(58) Field of Classification Search
CPC ..................... A61M 16/0816; A61M 16/1055; A61M 16/107; A61M 16/0858; A61M 16/1065
USPC ............. 128/200.24, 201.13, 202.27, 204.15, 128/204.17, 205.27, 205.29, 911, 912
See application file for complete search history.

(56) References Cited

U.S. PATENT DOCUMENTS

| | | | |
|---|---|---|---|
| 4,265,235 A | | 5/1981 | Fukunaga |
| 5,213,096 A | * | 5/1993 | Kihlberg et al. ......... 128/205.12 |
| 5,284,160 A | * | 2/1994 | Dryden ................... 128/203.12 |
| 5,390,668 A | * | 2/1995 | Lehman ................... 128/205.27 |
| 5,722,391 A | * | 3/1998 | Rosenkoetter et al. .. 128/200.24 |
| 5,894,839 A | * | 4/1999 | Rosenkoetter et al. .. 128/200.24 |
| 5,901,705 A | * | 5/1999 | Leagre ..................... 128/207.14 |
| 5,983,896 A | | 11/1999 | Fukunaga et al. |
| 6,363,930 B1 | * | 4/2002 | Clawson et al. ......... 128/201.13 |
| 6,508,249 B2 | | 1/2003 | Hoenig ..................... 128/202.27 |
| 6,733,556 B1 | * | 5/2004 | Luigi ............................ 55/385.1 |
| 7,140,366 B2 | * | 11/2006 | Smith et al. ............. 128/203.16 |
| 7,178,521 B2 | * | 2/2007 | Burrow et al. ........... 128/202.27 |
| 7,322,566 B2 | * | 1/2008 | Anthony ........................ 261/128 |
| 7,347,203 B2 | * | 3/2008 | Marler et al. ............ 128/201.13 |
| 7,594,509 B2 | * | 9/2009 | Burk ........................ 128/205.24 |
| 7,921,846 B1 | * | 4/2011 | Marler et al. ............ 128/205.24 |
| 2007/0163600 A1 | * | 7/2007 | Hoffman ................. 128/207.18 |

* cited by examiner

*Primary Examiner* — Annette Dixon
(74) *Attorney, Agent, or Firm* — McDermott Will & Emery LLP

(57) ABSTRACT

A respiratory connector for connecting an inspiratory tube and an expiratory tube to a coupling point of a medical apparatus is disclosed here. The respiratory connector includes a base element and two channels inside the base element, one of the channels is for an inspiratory flow and another is for an expiratory flow. The respiratory connector also includes a first sealable zone for sealing the base element with the coupling point and a second sealable zone at a distance from the first sealable zone for sealing with the coupling point. Both channels at least partly extend inside the base element between the first sealable zone and the second sealable zone. An arrangement for connecting an inspiratory tube and an expiratory tube to a medical apparatus is also disclosed.

20 Claims, 5 Drawing Sheets

RESPIRATORY CONNECTOR AND ARRANGEMENT FOR CONNECTING AN INSPIRATORY TUBE AND AN EXPIRATORY TUBE TO A MEDICAL APPARATUS

BACKGROUND OF THE INVENTION

This disclosure relates generally to a respiratory connector and an arrangement for connecting an inspiratory tube and an expiratory tube to a medical apparatus.

Conventional anesthesia machines and critical care ventilators are connected to a patient by means of inspiratory and expiratory tubes, which tubes can be side by side or as today more often coaxial. The reason to use coaxial tubes is that in that case expiration gas warms inspiration gas making breathing more pleasant for the patient. Usually an expiration air is flowing along an outer tube from the patient towards the machine and an inspiration air is flowing along an inner tube from the machine to the patient, whereby a warming of the inspiration air can be maximized and avoid cooling due to a lower room temperature. At machine end inspiratory and expiratory tubes need to be connected by a hospital personnel to the anesthesia machine or the ventilator preventing expiration and inspiration gases to be mixed. The aim is to use connectors, which are easy to use and safe. The working space in an operating room is limited and the personnel would like to minimize the amount of separate cables between patient and equipment.

While using coaxial inspiration and expiration tubes a connector is usually more complicated than when using tubes, which are side by side. One known solution is to direct an expiration flow coming from the patient along the outer coaxial tube to guide to a different route at the machine end of the connector than an inspiration air coming from the machine to the connector. This also means that the hospital personnel has to connect separately both the inspiration end of the connector to the machine and the expiration end of the connector and make sure the connections are tight enough to avoid leaking to the room air or from the room air to especially the inspiration air. This is too complicated and time consuming.

A newer approach while using coaxial breathing tubes is to avoid using different routes for inspiration and expiration gases inside the connector at the machine end, whereby the inspiration and expiration channels have a common coaxial machine end. This end will be connected to an adapter having coaxial channels for the inspiration and expiration air, but which channels inside the adapter guide these flows into different routes. The adapter is connected to a side of the machine and does not need to be detached, but instead can be used with many patients contrary to the connector which must be sterilized or which must be replaced with a new one. However, the adapter and the connector constitute a long device protruding from the side of the machine making it clumsy and vulnerable to users' pushes which may even cause a dangerous situation.

Also the more connections have to be made the more leaks and unintentional disconnections can appear. Especially a leak between inspiratory and expiratory line may be hazardous to the patient, because the patient may re-breathe carbon dioxide. Further a disadvantage is that the user has to use both hands when connecting the connector at the machine end to the adapter, because the user has to hold in one of his/her hands the adapter and simultaneously in another hand the connector and to push the connector strongly towards the adapter to make both the inspiration and expiration channels' joints tight to avoid leakages. From mechanical perspective, the manufacturing of a reliable connector with two coaxial conical surfaces is very challenging. Especially with reusable parts the wearing of the sealing surfaces may cause these conical connectors not to be reliably sealing simultaneously. Also the molding tools wear and may cause similar risks. Typically, a ventilator can detect a leak in the breathing circuit if the gases are leaking out of the circuit. However, a leak between the inner and outer channel of coaxial tubing is much more difficult to detect, especially without separate patient gas monitoring.

BRIEF DESCRIPTION OF THE INVENTION

The above-mentioned shortcomings, disadvantages and problems are addressed herein which will be understood by reading and understanding the following specification.

In an embodiment, a respiratory connector for connecting an inspiratory tube and an expiratory tube to a coupling point of a medical apparatus includes a base element and two channels inside the base element, one of the channels is for an inspiratory flow and another is for an expiratory flow. The respiratory connector also includes a first sealable zone for sealing the base element with the coupling point and a second sealable zone at a distance from the first sealable zone for sealing with the coupling point. Both channels at least partly extend inside the base element between the first sealable zone and the second sealable zone.

In another embodiment, a respiratory connector for connecting an inspiratory tube and an expiratory tube to a coupling point of a medical apparatus includes a base element and two channels inside the base element, one of the channels is for an inspiratory flow and another is for an expiratory flow and which channels have ventilator ends and tube ends, the ventilator ends being in flow connection with the coupling point of the medical apparatus and the tube ends being connectable with respective tubes, so that the channel for the inspiratory flow is adapted to be connected to the inspiratory tube and the channel for expiratory flow is adapted to be connected to the expiratory tube, and that the ventilator ends are located at a distance from each other. The respiratory connector also includes a first sealable zone around the base element for sealing with the coupling point to separate outside gas and one of the inspiratory flow or the expiratory flow and a second sealable zone for sealing with the coupling point to separate the inspiratory flow flowing through one of the ventilator ends and the respiratory flow flowing through another ventilator end. Both channels at least partly extend inside the base element between the first sealable zone and the second sealable zone.

In yet another embodiment, an arrangement for connecting an inspiratory tube and an expiratory tube to a medical apparatus includes a coupling point having a wall defining a hollow with at least an inspiratory port and an expiratory port and which coupling point is adapted to be connected to the medical apparatus. The arrangement for connecting an inspiratory tube and an expiratory tube to a medical apparatus also includes a respiratory connector insertable into the hollow of the coupling point, the respiratory connector including two channels, one of the channels is for an inspiratory flow and another of the channels is for an expiratory flow and which channels have ventilator ends and tube ends, the ventilator ends are adapted to be in flow connection with the coupling point, and the tube ends are adapted to be in flow connection with the respective inspiratory and expiratory tubes.

Various other features, objects, and advantages of the invention will be made apparent to those skilled in art from the accompanying drawings and detailed description thereof.

DETAILED DESCRIPTION OF THE INVENTION

Figure 1:
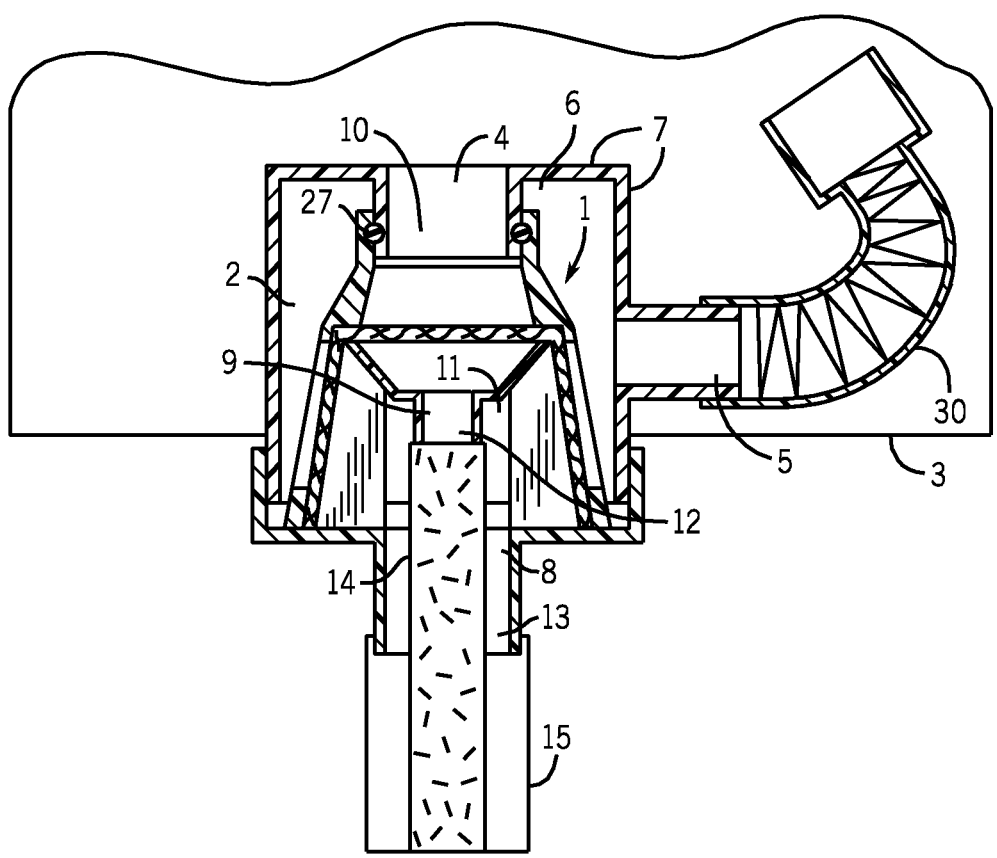
FIG. 1 is a cross-sectional view of a respiratory connector of an embodiment connected to a coupling point of a medical apparatus.

FIG. 1 shows a respiratory connector 1 connected to a coupling point 2 included in a medical apparatus 3 such as an anesthesia machine or a ventilator. The coupling point 2 is inside the medical apparatus 3 in FIG. 1, but as well it can be outside the medical apparatus 3, too. Further the coupling point 2 can be an integral part of the medical apparatus 3 especially if the coupling point 2 is inside the medical apparatus 3 or detachable especially in case the coupling point 2 is outside the medical apparatus 3. The coupling point 2 comprises two ports, one of which ports is an inspiratory port 4 and another is an expiratory port 5. The inspiratory port 4 is for guiding an inspiratory flow from the medical apparatus 3 towards the respiratory connector 1 and further to a patient (not shown). The expiratory port 5 is for guiding an expiratory flow coming from the patient through the respiratory connector 1 to the medical apparatus 3. The coupling point 2 includes a hollow 6 surrounded by a wall 7 having those inspiratory port 4 and expiratory port 5 and just this hollow 6 receives the respiratory connector 1 when it is pushed towards the coupling point 2. Advantageously the inspiratory port 4 is on the part of the wall 7, which is perpendicular to the direction of the respiratory connector 1 when pushing it towards the coupling point 2. Correspondingly the expiratory port 5 locates on the wall 7, which expiratory port 5 is crosswise in relation to the direction of the respiratory connector 1 when pushing it towards the coupling point 2. Naturally the locations of the expiratory port 5 and the inspiratory port 4 can be changed with each other or their locations can be changed to any suitable location of the coupling point 2.

The respiratory connector 1 shown in FIG. 1 includes two channels 8, 9. The channel 8 is for the expiratory flow coming from the patient towards the medical apparatus 3 and the channel 9 is for the inspiratory flow coming from the medical apparatus 3 towards the patient. The channel 9 is inside the channel 8, but it is quite possible to assemble the channel 8 inside the channel 9. The channels 8, 9 can also be coaxial. These channels 8,9 have ventilator ends 10, 11, the ventilator end 10 for the inspiratory flow being connectable to the inspiratory port 4 and the ventilator end 11 for the expiration flow being connectable to the expiratory port 5. The ventilator ends 10,11 are non-concentric with each other and have opening angles varying from each other. The ventilator end 11 which is crosswise, actually 90 degrees, in relation to the channels' 8, 9 direction. Or alternatively both ventilator ends 10, 11 open crosswise in relation to the direction of the respiratory connector 1 when pushing it towards the coupling point 2. Also the channels 8, 9 have tube ends 12, 13, the tube end 12 for the inspiratory flow being connectable to an inspiratory tube 14 and the tube end 13 for the expiratory flow being connectable to an expiratory tube 15. Both connections at the tube ends 12, 13 and the ventilator ends 10, 11 should be gas-tight. Usually the expiratory tube 15 between the patient and the respiratory connector 1 and the inspiratory tube 14 between the respiratory connector 1 and the patient are made of a flexible material, which can easily form a gas-tight connection with the channels 8, 9 made advantageously of a rigid material. The inspiratory and expiratory tubes 14, 15 can be coaxial, too.

Figure 2:
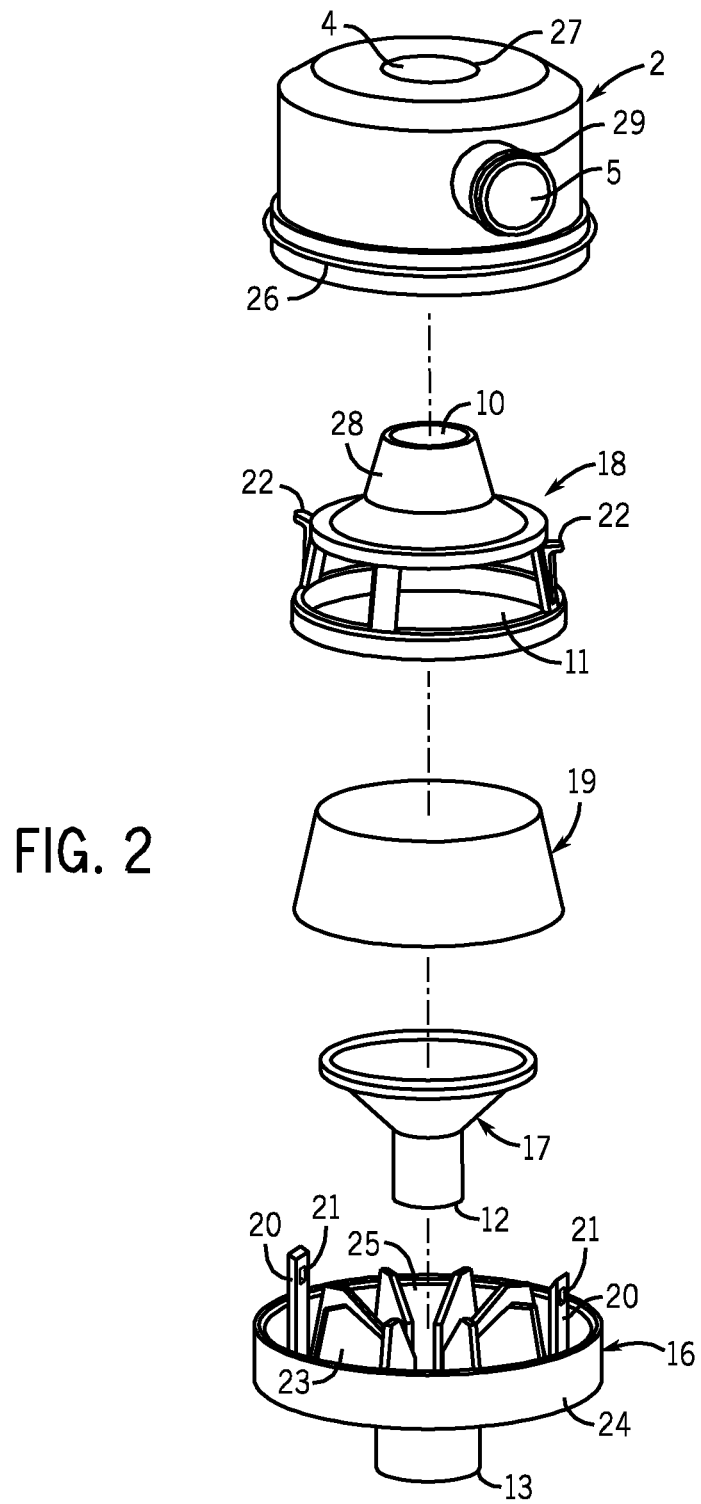
FIG. 2 is an exploded view of the respiratory connector together with the coupling point in accordance with an embodiment.

FIG. 2 shows details of the respiratory connector 1 comprising components such as a base element 16, a flow guide 17 and a flow separator 18. These three components could be made of one single piece, but it is more practical to use different components especially in case a filter element 19 for filtering the breathing air of the patient is included inside the respiratory connector 1. In this specific embodiment the filter element 19 is one single piece for filtering both the expiratory flow and the inspiratory flow. The filter element 19 can be made for filtering e.g. bacteria and prevent any harmful contaminations beyond the other side of the filter element 19.

The flow guide 17 is to guide the inspiratory and expiratory gas flows inside the respiratory connector 1. In this embodiment of FIG. 2 the flow guide 17 is shaped as a funnel having the tube end 12. Another tube end 13 is a part of the base element 16. These tube ends 12, 13 are connectable to the inspiratory tube 14 and the expiratory tube 15 as explained above and this connection can be made before the flow guide 17 is coupled together with the base element 16 or afterwards especially in case the tube end 12 extends beyond the other tube end 13.

The base element 16 includes a fixing element 20 with a hole 21 for fixing with the flow separator 18 having a counterpart 22 pushing to the hole 21 while coupling together leaving both the flow guide 17 and the filter element 19 therebetween as shown in FIG. 2. Depending on the structure one or more fixing elements 20 are needed. The base element 16 includes flanges 23 for receiving the flow guide 17 while collecting the respiratory connector 1 and keeping the flow guide 17 in the right position when collected. Further a projection 24 encircles the base element 16 and which projection 24 can be used to form a first sealable zone 25 on the surface of the projection 24 for sealing with the coupling point 2 of the medical apparatus 3 when the respiratory connector 1 is connected to this coupling point 2. The first sealable zone 25 separates outside gas from one of the inspiratory flow and the expiratory flow.

The flow separator 18 includes the ventilator ends 10, 11 needed while connecting the respirator connector 1 to the coupling point 2 as explained above. The ventilator end 11 according to FIG. 2 embodiment opens 360 degrees around the flow separator 18 making possible to exploit a large filtration area of the filter element 19 and thus extending its operating time. Also the other ventilator end 10 is designed so that a large filtration area of the filter element 19 can be exploited for same reasons.

FIG. 2 shows also the coupling point 2 having the inspiratory port 4 for the inspiratory gas flow and the expiratory port 5 for the expiratory gas flow. A periphery of the coupling point 2 is equipped with a first opposing sealable zone 26 such as a washer, which together with the first sealable zone 25 forms a gas-tight sealing when the respiratory connector 1 has been connected to the coupling point 2 separating a room air and the gas flow of the patient and thus preventing them from mixing. The inspiratory port 4 having a second opposing sealable zone 27 of the coupling point 2 is adapted to make a gas-tight sealing with a second sealable zone 28 separating the inspiratory flow flowing through one of the ventilator ends 10 or 11 and expiratory flow flowing through another ventilator end 10 or 11 and thus preventing these flows from mixing. The second sealable zone 28 encircles the surface of the flow separator 18 at the ventilator end 10 of the channel 9 and is preferably conical. Further the expiratory port 5 is equipped with a third sealable zone 29 for making a gas-tight connection with the ventilator channel 30 as shown in FIG. 1 which may be a flexible or elastic tube. According to the embodiment the first sealable zone 25 of the base element 16 and the second sealable zone 28 are at a distance from each other and between the first sealable zone 25 and the second sealable zone 28 there is the ventilator end 11 which is crosswise in relation to one of the channel's 8, 9 direction or alternatively in relation to the direction of the respiratory connector 1 when pushing it towards the coupling point 2. Both said channels 8, 9 at least partly extend between said first sealable zone 25 and said second sealable zone 28 inside said base element 16. Also the ventilator end 11 is crosswise in relation to another ventilator end 10. In this connection it important to understand instead of the ventilator end 11 for the expiration flow there could be the ventilator end 10 for the inspiration flow between the first sealable zone 25 and the second sealable zone 28 if so desired.

When connecting the respiratory connector 1 and the coupling point 2, a tip of the respiratory connector 1 with the second sealable zone 28 is first inserted into the hollow 6 of the coupling point 2 approaching the second opposing sealable zone 27 of the inspiratory port 4 of the coupling point 2. Simultaneously the first sealable zone 25 of the respiratory connector 1 is approaching the first opposing sealable zone 26 around the periphery of the coupling point 2. It is advantageous to arrange both sealings to happen simultaneously even though it is possible to make these sealings in succession.

Figure 3:
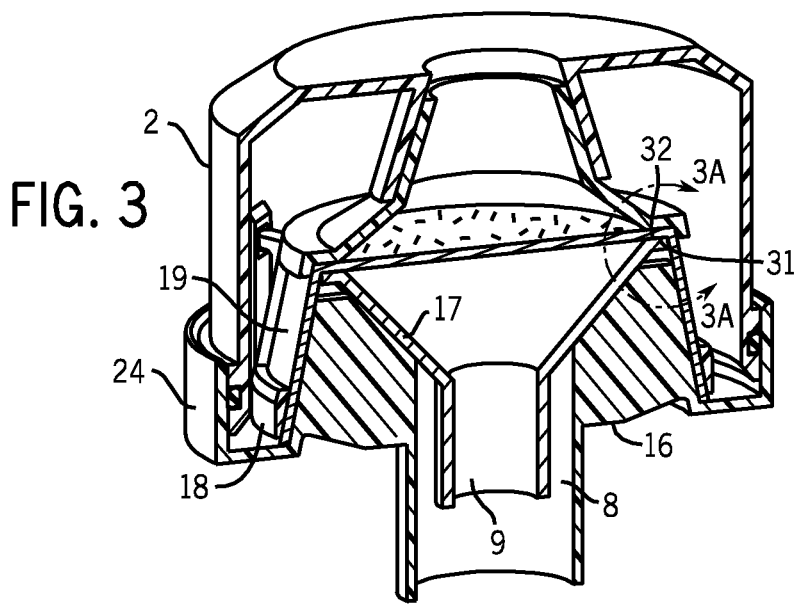
FIG. 3 is a cross-sectional view of the respiratory connector connected to the coupling point shown in FIG. 2.
Figure 3A:
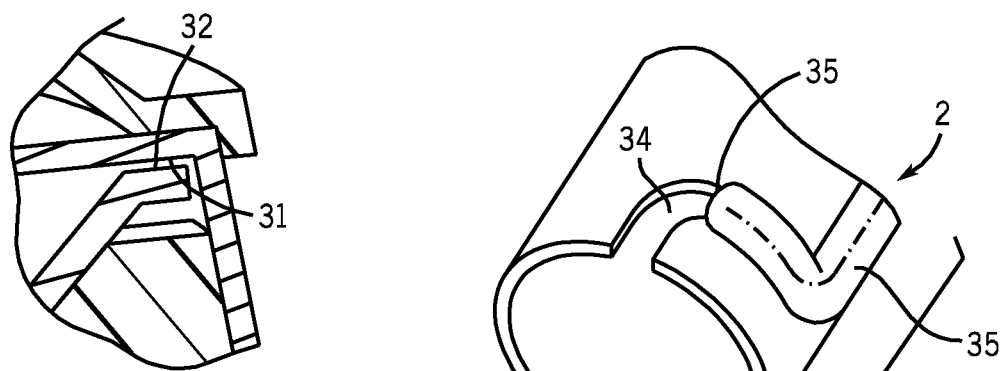
FIG. 3A is a partial enlargement of FIG. 3.

A cross-sectional view of the respiratory connector 1 is shown in FIG. 3 when connected to the coupling point 2 of the medical apparatus 3. The base element 16, the flow guide 17, the filter element 19 and the flow separator 18 are assembled and connected to the coupling point 2. The flow guide 17 is pressed towards the flow separator 18 leaving the filter element 19 therebetween and thus forming a sealing between first contact surface 31 of the flow separator 18 and a second contact surface 32 of the flow guide 17 as shown in FIG. 3A, which is a partial enlargement of FIG. 3. This arrangement prevents inspiratory flow flowing along channel 9 and the expiratory flow flowing along the channel 8 from mixing together.

Figure 4:
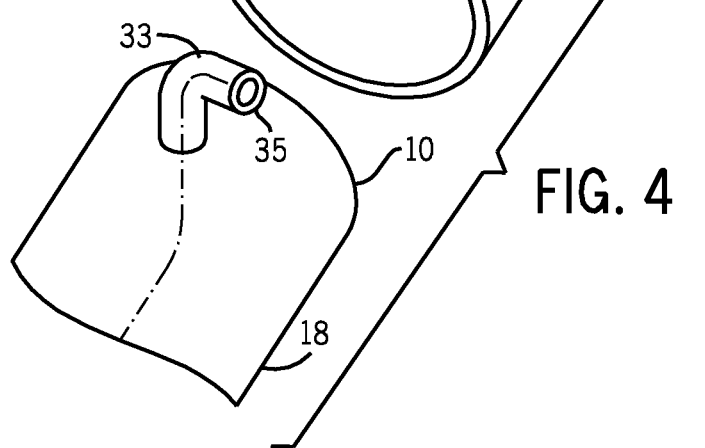
FIG. 4 is an enlarged view of an additional detail of the respiratory connector and the coupling point of the medical apparatus.

FIG. 4 shows a feature useful when connecting the respiratory connector 1 to the coupling point 2 of the medical apparatus 3. There is a pin 33 projecting from either the flow separator 18 as shown in the FIG. 4 or alternatively from the coupling point 2 and a receiver 34 such as a slot correspondingly either in the coupling point 2 as shown in the FIG. 4 or alternatively in the flow separator 18. When connecting the respiratory connector 1 to the coupling point 2 the pin 33 contacts the receiver 34 guiding it and making the connection secure. Further the pin 33 and the receiver 34 may include a sample line 35 connecting them simultaneously while making the connection between the respiratory connector 1 and the coupling point 2. The sample line 35 can be used e.g. to draw fluid samples from the patient to an analyzer (not shown) whereby no separate sample line is needed. Also the sample line 35 can be understood to be a pressure line to measure pressure or even to include two different pressure lines for measuring pressure difference. Further the sample line 35 can be an electric contact and be e.g. connected to electrodes for measuring EEG or EMG from the patient's head.

Figure 5:
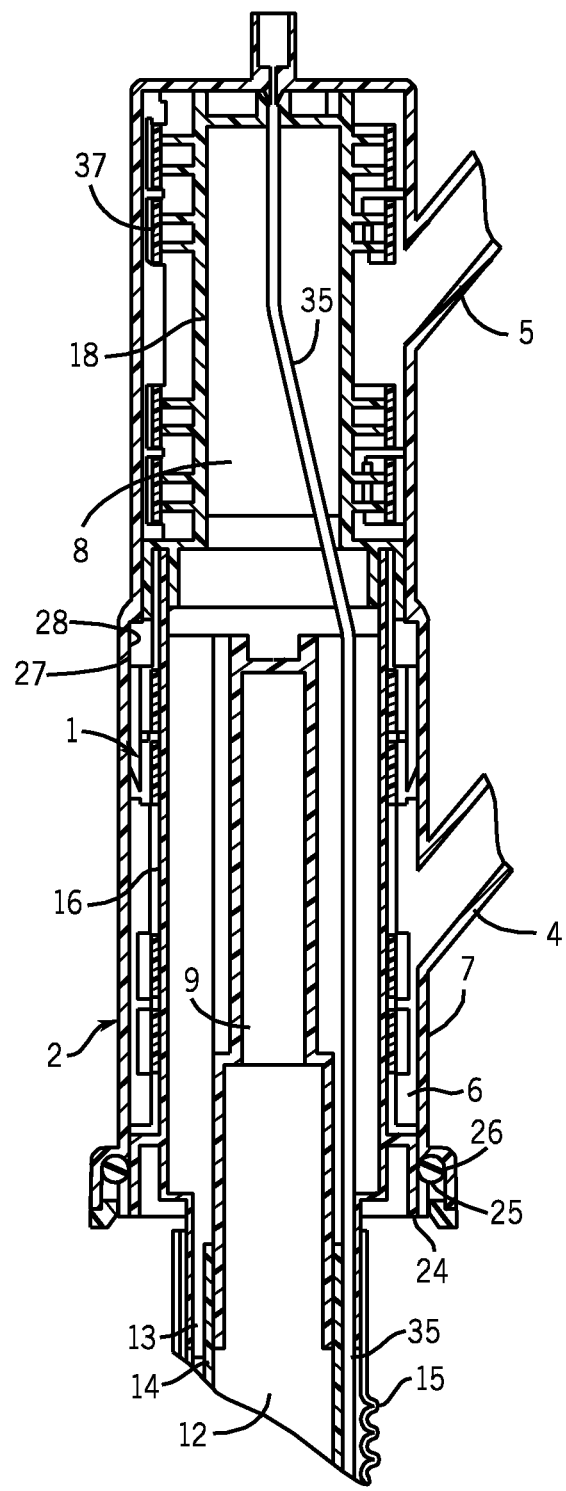
FIG. 5 is a cross-sectional view of a respiratory connector of another embodiment connected to a coupling point of the medical apparatus.
Figure 6:
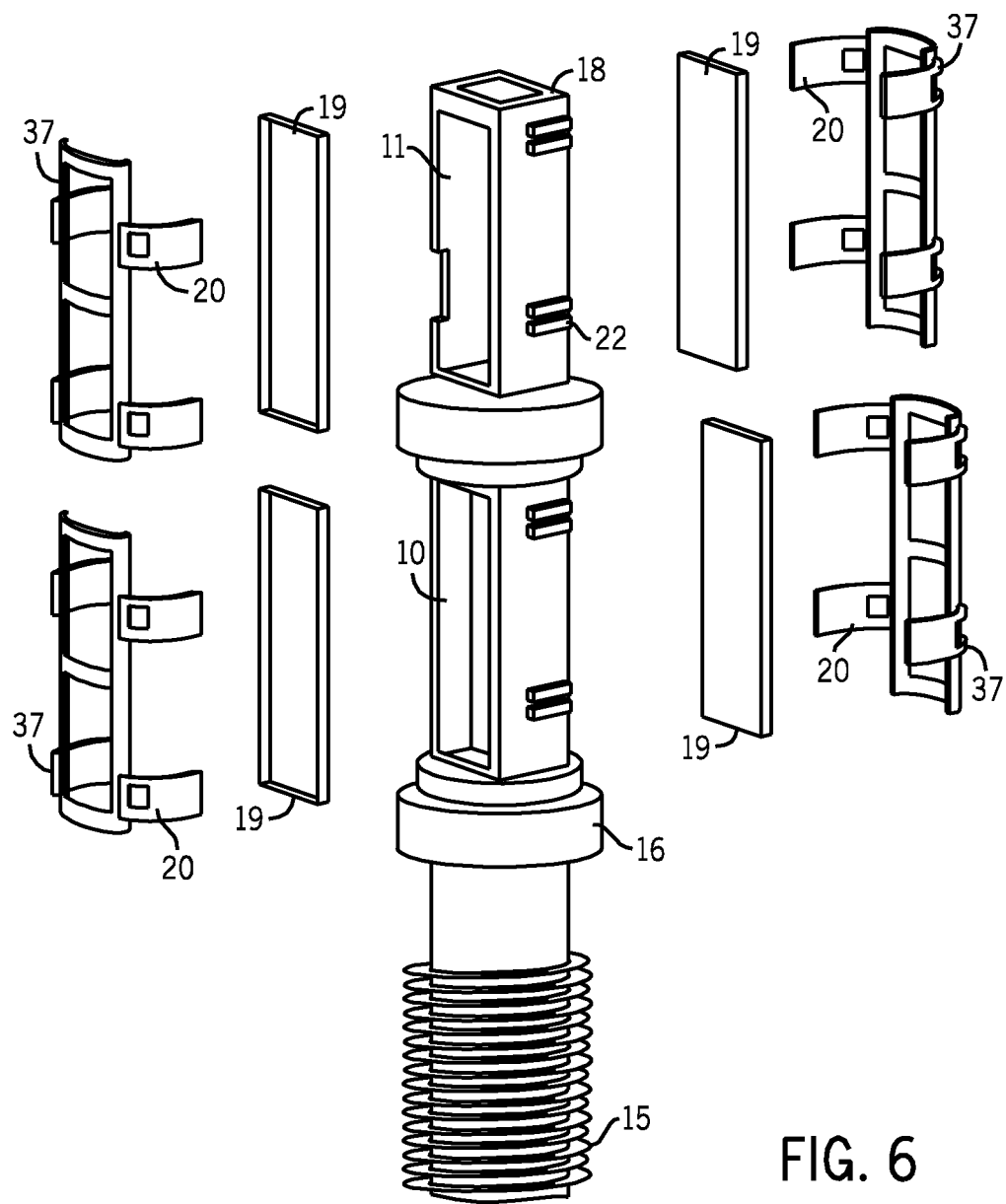
FIG. 6 is an exploded view of the respiratory connector shown in FIG. 5.

Another embodiment using same reference numbers as with previous embodiments is shown in FIG. 5 where the respiratory connector 1 is connected to the coupling point 2 having the hollow 6. FIG. 6 shows an exploded view of the respiratory connector 1 of FIG. 5 and both figures are referred while explaining its structure below. The base element 16 is coupled e.g. glued to the flow separator 18, so that one of the channels 8, 9 extends inside the flow separator 18 and that both two channels 8, 9 extend inside the base element 16. In this specific embodiment the expiration air is flowing inside this flow separator 18 including the ventilator end 11 for the expiration air, too. The ventilator end 10 for the inspiration air is in the base element 16. However, the flow separator 18 could be a part of the base element 16 and thus be one single piece, but it is probably cheaper to make two different pieces.

A remarkable difference of FIG. 5 and 6 with the previous embodiment shown in FIGS. 1, 2 and 3 is that both ventilator ends 10, 11 are parallel and open crosswise, actually 90 degrees, in relation to the channels' 8, 9 direction. Or alternatively both ventilator ends 10, 11 open crosswise in relation to the direction of the respiratory connector 1 when pushing it towards the coupling point 2. The ventilator ends 10, 11 are non-concentric just as in previous embodiments, too. There are separate filter elements 19 for the inspiratory flow and the expiratory flow. FIG. 6 even shows two separate filter elements 19 on both sides of each channel 8, 9 for both the inspiratory flow and the expiratory flow. Each filter element 19 is assembled between a support element 37 and either the inspiratory port 4 or the expiratory port 5. The support element 37 has one or more fixing element 20 connectable correspondingly to one or more counterpart 22 of the base element 16 or the flow separator 18.

As sown in FIG. 5 the base element 16 is encircled by the projection 24 forming the first sealable zone 25 on the surface of the projection 24 allowing the gas-tight connection with the first opposing sealable zone 26 of the coupling point 2. Both the channel 9 for the inspiratory flow and the channel 8 for the expiratory flow inside the base element 16 extend between the first sealable zone 25 and the ventilator ends 10, 11 for the inspiratory flow and the expiratory flow. The second sealable zone 28 encircles the surface of the flow separator 18 and the second opposing sealable zone 27 on the wall 7 of the coupling point 2 forms a gas-tight sealing when the respiratory connector 1 has been connected to the coupling point 2 thus separating the inspiratory and the expiratory flows and preventing these flows from mixing. The first sealable zone 25 of the base element 16 and the second sealable zone 28 of the flow separator 18 are at a distance from each other. Between the first sealable zone 25 and the second sealable zone 28 there is the ventilator end 10 which is crosswise in relation to one of the channel's 8, 9 direction or alternatively in relation to the direction of the respiratory connector 1 when pushing it towards the coupling point 2. Also the ventilator end 10 is parallel in relation to another ventilator end 11. In this connection it is important to understand that it is all the same to the embodiment whether the expiratory flow goes through the ventilator end 11 or 10 depending on which one of the channels 8, 9 has been reserved for the expiratory flow and correspondingly for the inspiratory flow. Both the expiratory port 5 and the inspiratory port 4 of the coupling point 2 are on the part of the wall 7, which is crosswise in relation to one of the channel's 8, 9 direction or which is crosswise in relation to the direction of the respiratory connector 1 when pushing it towards the coupling point 2.

The sample line 35 discussed with FIG. 4 is shown in FIG. 5, too, extending through the respiratory connector 1 and is located inside the channel 8, but could as well locate inside the channel 9, too. The sample line 35 ends at the end of the flow separator 18 where it is connected to the medical apparatus 3 receiving samples, when the respiratory connector 1 is connected to the coupling point 2.

An advantage of embodiments discussed above is that the respiratory connector 1 can be connected to the coupling point 2 of the medical apparatus 3 only using one hand for this purpose. This is because the user simply needs to push the respiratory connector 1 to the coupling point 2 coupled to the medical apparatus 3. Provided that the coupling point 2 is firmly coupled to the medical apparatus 3 it makes the coupling even easier, because the machine is rather steady. This is possible with the respiratory connector 1 including the first sealable zone 25 and the second sealable zone 28 at the distance from each other whereby the first sealable zone 25 can be at a rear of the respiratory connector 1 and the second sealable zone 28 in the front part of the respiratory connector 1. Between the first sealable zone 25 and the second sealable zone 28 there is the ventilator end 10 or 11 for allowing the flow between the respirator connector 1 and the medical apparatus 3 when the respirator connector 1 is connected to the coupling point 2. An important thing is to have this kind of the respiratory connector 1 which can be inserted inside the hollow 6 of the coupling point 2 and which hollow 6 is surrounded by a wall 7 having those inspiratory port 4 and expiratory port 5. The hollow 6 also guides an insertion of the respiratory connector 1 making the coupling user-friendly. This arrangement when especially the coupling point 2 is partly or in whole inside the medical machine 3 makes possible to insert the respiratory connector 2 according to the embodiments inside the coupling point 2 for not protruding disturbingly from the medical apparatus 3.

Additional advantage is that the respiratory connector 1 can be equipped with the coupling point 2 already in a factory in case a customer has the medical apparatus 3 without any compatible coupling point for the respiratory connector 1. In this case the customer can simply connect the inspiratory port 4 and the expiratory port 5 of the coupling point 2 to corresponding gas channels of the medical apparatus 3. Or the customer can remove the coupling point 2 supplied with the respiratory connector 1 and connect the respiratory connector 1 directly to the existing compatible coupling point 2. Further advantage is that the embodiments of the respiratory connector 1 are rather easy and cheap to manufacture. When the ventilator ends 10, 11 are non-coaxial and especially when only one of the first sealable zone 25 and the second sealable zone 27 is conical and the other one is non-conical equipped with e.g. o-ring or similar, the mechanism can better cope with manufacturing tolerance deviations and wear during the use.

The written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A respiratory connector for connecting an inspiratory tube and an expiratory tube to a coupling point of a medical apparatus, comprising:
   a base element;
   two channels inside said base element and extending along a longitudinal axis, one of which said channels is for an inspiratory flow and another is for an expiratory flow such that the inspiratory flow is separated from the expiratory flow, the channels being in flow communication with respective ventilator ends, and at least one ventilator end being longitudinally oriented;
   at least one filter element adjacent to and covering the longitudinally oriented ventilator end;
   a first sealable zone for sealing said base element with said coupling point;
   a second sealable zone positioned a distance from said first sealable zone along the longitudinal axis for sealing the respiratory connector with said coupling point; and
   a flow separator, extending between the first sealable zone and the second sealable zone, the flow separator defining the longitudinally oriented ventilator end,
   wherein both said channels at least partly extend inside said base element between said first sealable zone and said second sealable zone.

2. The respiratory connector of claim 1, wherein said channels are in flow communication with respective tube ends, said ventilator ends being in flow communication with said coupling point of said medical apparatus and said tube ends being connectable with the inspiratory and expiratory tubes.

3. The respiratory connector of claim 2, wherein said ventilator ends are located non-concentrically with each other and at least one of said ventilator ends is open crosswise in relation to the longitudinal axis of the two channels.

4. The respiratory connector of claim 2, wherein said ventilator ends have opening angles varying from each other.

5. The respiratory connector of claim 4, wherein said ventilator ends have opening angles varying from each other about 90 degrees.

6. The respiratory connector of claim 2, wherein said ventilator ends are parallel.

7. The respiratory connector of claim 6, wherein said ventilator ends are non-concentric and have openings crosswise in relation to the longitudinal axis of the two channels.

8. The respiratory connector of claim 2, wherein said both channels inside said base element extend beyond said first sealable zone towards said ventilator ends and a first sealable zone is to separate outside gas and one of the inspiratory flow or the expiratory flow.

9. The respiratory connector of claim 2 further comprising a flow guide to guide the inspiratory and expiratory flows, wherein the at least one filter element filters one of inspiratory flow or expiratory flow, wherein the flow separator defines said ventilator ends and the flow guide and the at least one filter element are pressed between said flow separator and said base element.

10. The respiratory connector of claim 9 wherein the flow separator comprises one of said ventilator ends and which flow separator is adapted to be coupled to said base element comprising another of said ventilator ends and filter elements for said ventilator ends.

11. The respiratory connector of claim 2 further comprising a pin to ensure secure connection between said respiratory connector and said coupling point of the medical apparatus.

12. The respiratory connector of claim 2, wherein said coupling point is a hollow surrounded by a wall having two ports for connecting to said ventilator ends of respective channels for inspiratory flow and expiratory flow.

13. The respiratory connector of claim 1, wherein said second sealable zone is adapted to separate the expiratory flow and the inspiratory flow when coupled to said coupling point.

14. The respiratory connector of claim 1 further comprising a sample line for taking gas samples, measuring pressure, measuring pressure difference or transmitting electrical signals.

15. A respiratory connector for connecting an inspiratory tube and an expiratory tube to a coupling point of a medical apparatus, comprising:
 a base element;
 two channels inside said base element each extending along a longitudinal axis, one of which said channels is for an inspiratory flow and another is for an expiratory flow and which channels are in flow connection with respective ventilator ends and respective tube ends, at least one ventilator end being longitudinally oriented, said ventilator ends being in flow connection with said coupling point of said medical apparatus and said tube ends being connectable with the inspiratory and expiratory tubes, so that said channel for the inspiratory flow is adapted to be connected to said inspiratory tube and said channel for expiratory flow is adapted to be connected to said expiratory tube, and that said ventilator ends are located at a distance from each other along the longitudinal axis;
 at least one filter element adjacent to and covering the longitudinally oriented ventilator end;
 a first sealable zone around said base element for sealing with said coupling point to separate outside gas and one of the inspiratory flow or the expiratory flow;
 a second sealable zone for sealing the respiratory connector with said coupling point to separate the inspiratory flow flowing through one of the ventilator ends and the respiratory flow flowing through another ventilator end;
 a flow separator between the first sealable zone and the second sealable zone, the flow separator defining the longitudinally oriented ventilator end; and
 wherein both said channels at least partly extend inside said base element between said first sealable zone and said second sealable zone.

16. The respiratory connector of claim 15, wherein said at least one ventilator end is crosswise in relation to the longitudinal axis.

17. The respiratory connector of claim 15, wherein said ventilator ends are located non-concentrically with each other.

18. An arrangement for connecting an inspiratory tube and an expiratory tube to a medical apparatus, comprising:
 a coupling point having a wall defining a hollow with at least an inspiratory port and an expiratory port and which coupling point is adapted to be connectable to said medical apparatus;
 a respiratory connector insertable into said hollow of said coupling point, said respiratory connector including two channels extending along a longitudinal axis, one of said channels is for an inspiratory flow and another of said channels is for an expiratory flow and which channels are in flow connection with respective ventilator ends and respective tube ends, at least one ventilator end being longitudinally oriented, said ventilator ends are adapted to be in flow connection with said coupling point, and said tube ends are adapted to be in flow connection with said respective inspiratory and expiratory tubes;
 a flow separator defining the longitudinally oriented ventilator end; and
 a filter element adjacent to and covering the longitudinally oriented ventilator end.

19. The respiratory connector of claim 18, wherein said respiratory connector, which is detachably insertable into said hollow of said coupling point, includes a base element with said two channels inside said base element and a first sealable zone around said base element for sealing with said coupling point to separate outside gas and one of the inspiratory flow or the expiratory flow.

20. The respiratory connector of claim 19 further comprising a second sealable zone at a distance along the longitudinal axis from said first sealable zone and for sealing with said coupling point, when said respiratory connector and said coupling point are connected, to separate the inspiratory flow flowing through one of the ventilator ends and the respiratory flow flowing through another ventilator end.

* * * * *